United States Patent
Choi et al.

(10) Patent No.: US 11,504,308 B2
(45) Date of Patent: *Nov. 22, 2022

(54) COSMETICS CONCEALING WRINKLES

(71) Applicant: LG Household & Health Care Ltd., Seoul (KR)

(72) Inventors: Minsung Choi, Daejeon (KR); Young-Sook Song, Daejeon (KR); Sun Gyoo Park, Daejeon (KR)

(73) Assignee: LG Household & Health Care Ltd.

( * ) Notice: Subject to any disclaimer, the term of this patent is extended or adjusted under 35 U.S.C. 154(b) by 27 days.

This patent is subject to a terminal disclaimer.

(21) Appl. No.: 17/339,548

(22) Filed: Jun. 4, 2021

(65) Prior Publication Data
US 2021/0290498 A1 Sep. 23, 2021

Related U.S. Application Data

(63) Continuation of application No. 16/089,780, filed as application No. PCT/KR2017/002743 on Mar. 14, 2017, now Pat. No. 11,058,614.

(30) Foreign Application Priority Data

Apr. 4, 2016 (KR) ........................ 10-2016-0041203

(51) Int. Cl.
*A61K 8/04* (2006.01)
*A61K 8/37* (2006.01)
(Continued)

(52) U.S. Cl.
CPC ................ *A61K 8/042* (2013.01); *A61K 8/06* (2013.01); *A61K 8/37* (2013.01); *A61K 8/89* (2013.01);
(Continued)

(58) Field of Classification Search
None
See application file for complete search history.

(56) References Cited

U.S. PATENT DOCUMENTS

2006/0159716 A1 7/2006 Themens et al.
2012/0269753 A1 10/2012 Rabe et al.
2013/0202665 A1 8/2013 Chiba et al.

FOREIGN PATENT DOCUMENTS

EP 2492333 A1 8/2012
EP 2556822 A1 2/2013
(Continued)

OTHER PUBLICATIONS

International Search Report From PCT/KR2017/002743 dated Jul. 12, 2017.
(Continued)

*Primary Examiner* — Kyung S Chang
(74) *Attorney, Agent, or Firm* — Lerner, David, Littenberg, Krumholz & Mentlik, LLP

(57) ABSTRACT

The present invention relates to a method for concealing wrinkles. The method for concealing wrinkles includes applying a cosmetic composition having an oil-wax gel for diffusing reflection of light at a wrinkled area to a skin, wherein the oil-wax gel is a gel comprising silicone oil and wax, wherein hardness of the oil-wax gel is 100 to 4000 dyn/cm$^2$, and wherein the oil-wax gel comprises 5 to 95 parts by weight of the silicone oil relative to 100 parts by weight of the oil-wax gel and 1 to 50 parts by weight of the wax relative to 100 parts by weight of the oil-wax gel.

12 Claims, 3 Drawing Sheets

(51) Int. Cl.
*A61K 8/89* (2006.01)
*A61K 8/891* (2006.01)
*A61K 8/895* (2006.01)
*A61K 8/92* (2006.01)
*A61Q 1/00* (2006.01)
*A61Q 19/08* (2006.01)
*A61K 8/06* (2006.01)
*A61Q 19/00* (2006.01)

(52) U.S. Cl.
CPC .............. *A61K 8/891* (2013.01); *A61K 8/895* (2013.01); *A61K 8/92* (2013.01); *A61Q 1/00* (2013.01); *A61Q 19/00* (2013.01); *A61Q 19/08* (2013.01)

(56) References Cited

FOREIGN PATENT DOCUMENTS

| | | | |
|---|---|---|---|
| JP | 2000007551 | A | 1/2000 |
| JP | 2002241215 | A | 8/2002 |
| JP | 2007023022 | A | 2/2007 |
| JP | 2010006781 | A | 1/2010 |
| JP | 2010047495 | A | 3/2010 |
| KR | 2008-0079033 | A | 8/2008 |
| KR | 101088955 | B1 | 12/2011 |
| KR | 101133098 | B1 | 4/2012 |
| KR | 20140004861 | A | 1/2014 |
| KR | 2014-0078149 | A | 6/2014 |
| KR | 2014-0099176 | A | 8/2014 |
| KR | 10-1664769 | B1 | 10/2016 |

OTHER PUBLICATIONS

Mai, Takeo, et al. "Relationship Between the Hardness of an Oil-Wax Gel and the Surface Structure of the Wax Crystals." Colloids and Surfaces A: Physicochemical and Engineering Aspects, 194 (2001) pp. 233-237.

Imai T, Nakamura K, Shibata M. Relationship between the hardness of an oil-wax gel and the surface structure of the wax crystals. Colloids and Surfaces A: Physicochemical and Engineering Aspects. Dec. 20, 2001;194(1-3):233-7.

Supplementary European Search Report including Written Opinion for EP17779281.9 dated Aug. 20, 2019.

[Fig. 1]
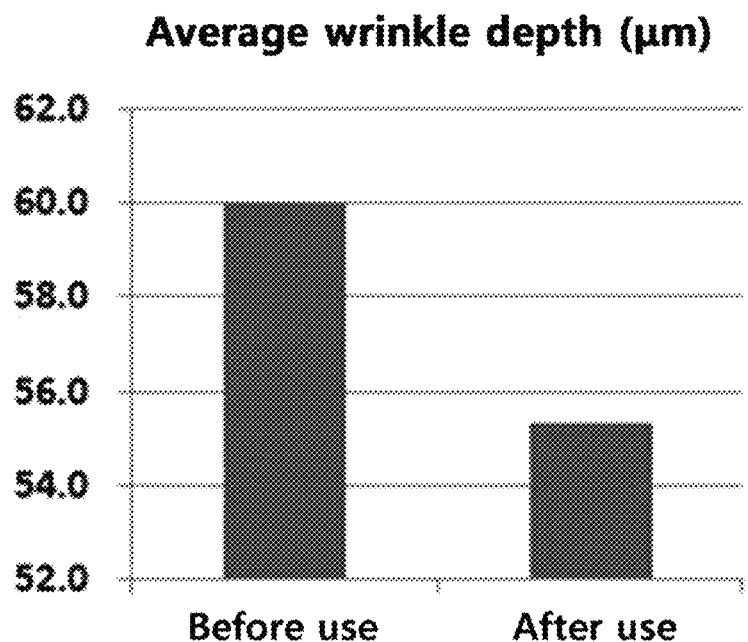
[Fig. 2]
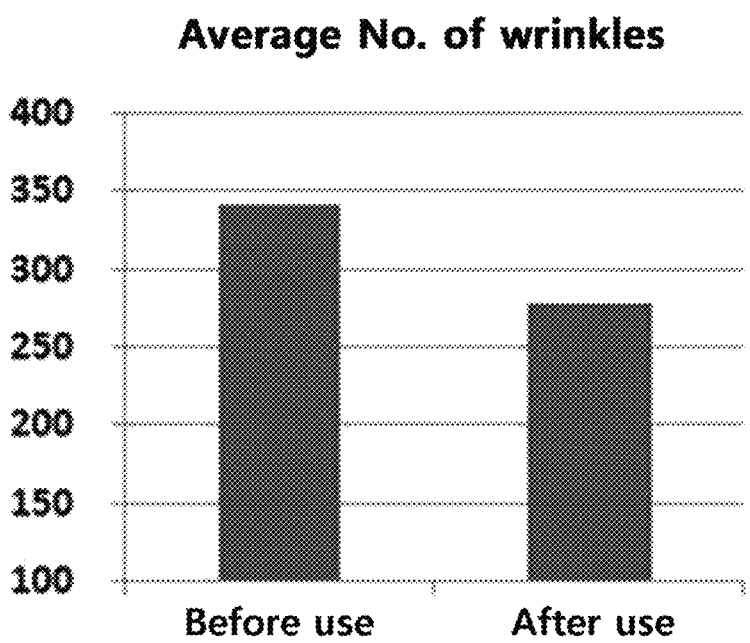

[Fig. 3]
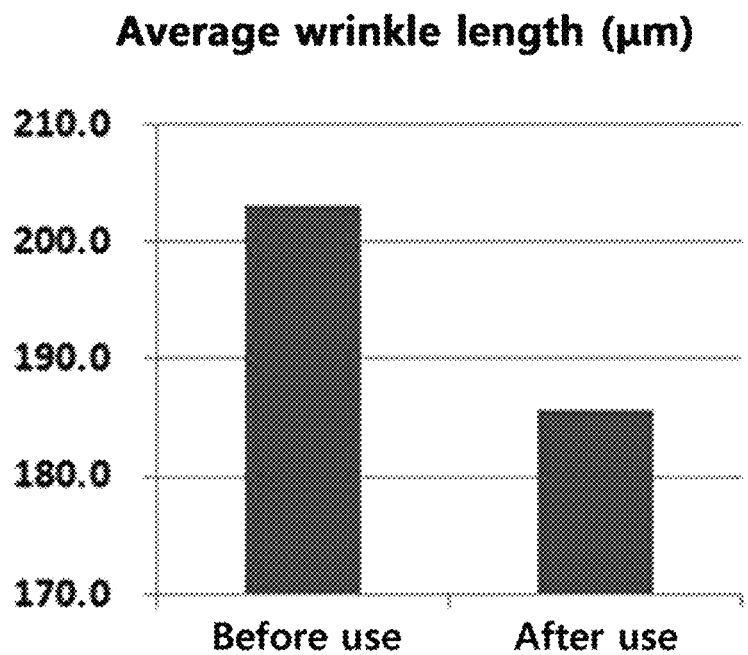
[Fig. 4]
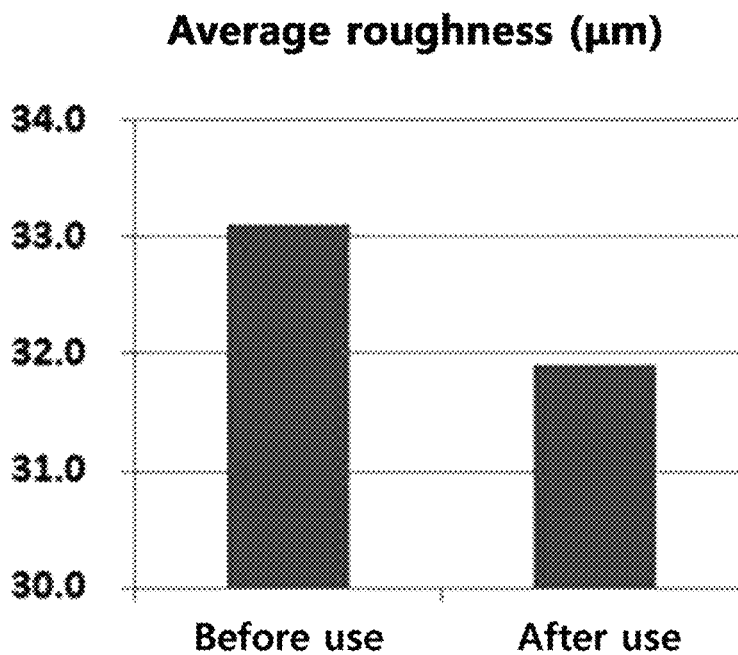

[Fig. 5]
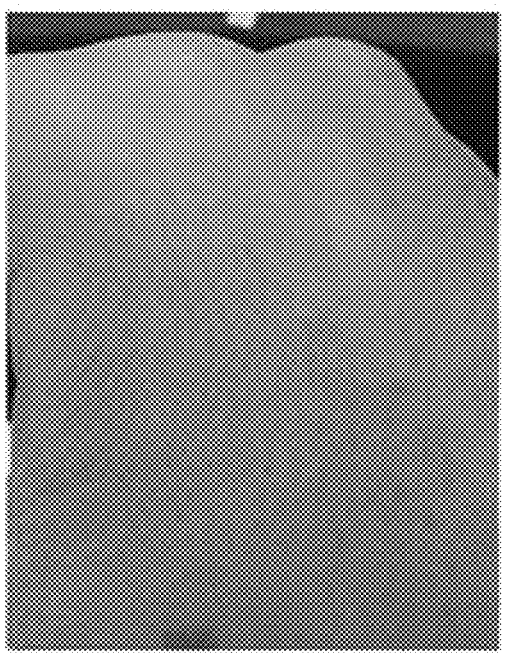 
Before use          After use

COSMETICS CONCEALING WRINKLES

CROSS-REFERENCE TO RELATED APPLICATIONS

This application is a continuation of U.S. application Ser. No. 16/089,780, filed Sep. 28, 2018, which is a national phase entry under 35 U.S.C. § 371 of International Application No. PCT/KR2017/002743, filed Mar. 14, 2017, which claims priority to Korean Patent Application No. 10-2016-0041203, filed Apr. 4, 2016, the disclosures of which are incorporated herein by reference.

TECHNICAL FIELD

The present invention relates to a cosmetic composition for concealing wrinkles.

BACKGROUND ART

Cosmetic products for improving wrinkles may be divided into a functional cosmetic product which acts on a wrinkle-causing factor to fundamentally eliminate wrinkles and a cosmetic product which fills in a wrinkled area by utilizing powder and conceals the wrinkles temporarily by causing diffuse reflection of light at the wrinkled area.

In the case of the cosmetic product which temporarily conceals the wrinkles on the wrinkled area, resulting in the diffuse reflection, its use has a limitation in that, since an excessive amount of powder is added, it causes a heavy and hard feeling of use and white turbidity when applied to skin. Additionally, due to moisture and oil absorbing nature of the powder, the skin becomes dry and adhesion to the skin weakens, causing the powder to agglomerate and not stick to the skin well. This makes it difficult to provide a prolonged effect.

Meanwhile, principle of the diffuse reflection of light is as follows. When a substance is irradiated with light, a part of the light is reflected from a surface and the other part is transmitted. At this time, the light is refracted at a particular angle depending on a refractive index of the substance and is then transmitted. When the light is irradiated on a substance in which very small particles are combined, a part of the light is reflected from the particle located on the surface of the substance, and the rest is refracted at a particular angle and then transmitted. The same phenomenon occurs when the transmitted light reaches a surface of a second particle inside the substance. However, the light reflected at the second particle surface is reflected at a different angle from that reflected at the first particle in accordance with a refractive index of the substance and an internal particle structure. When such phenomenon occurs consecutively between the particles located inside the substance, the reflected light is reflected at each of different angles of the particles, ultimately causing the diffuse reflection.

DISCLOSURE

Technical Problem

The present inventors have discovered a problem in a composition comprising powder. As a result of making extensive research efforts to develop a cosmetic composition which is easy to apply and has an excellent feeling of use while exhibiting a wrinkle-concealing effect, the present inventors have completed the present invention by confirming that when the cosmetic composition comprises an oil-wax gel comprising silicone oil and wax, it shows an excellent feeling of use and an instant wrinkle-concealing effect by causing diffuse reflection of light at a wrinkled area.

Technical Solution

An object of the present invention is to provide a cosmetic composition capable of concealing wrinkles by causing diffuse reflection of light at a wrinkled area without using powder, a cosmetic product comprising the same, and a method for concealing wrinkles comprising applying the composition to a skin.

Hereinbelow, the present invention will be described in detail.

As an aspect for achieving the above object, the present invention provides a cosmetic composition for concealing wrinkles, comprising an oil-wax gel comprising silicone oil and wax.

The diffuse reflection of light is a form of reflection of light which shows a visual concealing effect by the light reflected at different angles, whereas specular reflection, in contrast to the visual concealing effect, is a form of reflection of light in which incident light remains parallel after reflection. In order to provide a cosmetic composition for temporarily concealing wrinkles, it is indispensable to design a composition and a three-dimensional structure which can effectively induce the diffuse reflection of light.

In an existing cosmetic composition for a temporary wrinkle-concealing effect, powder was used to induce the diffuse reflection of light. However, the use of powder may cause white turbidity and deterioration of feeling of use when applied to the skin. In addition, adhesion to the skin during long-term use may be reduced.

An oil-wax gel refers to an oily solid composed of liquid oil and crystalline solid oil (I. Takeo, N. Koichi, and S. Masashi, Colloids and Surfaces A, 194, 233, 2001). More specifically, the oil wax gel is a gel in which oil is placed in the inner space of a three-dimensional structure formed by a combination of fine wax crystals. Not only may the hardness of such oil-wax gel vary according to a type of oil and a three-dimensional structure in which the wax forms, but optical characteristics such as a reflection type of light may also vary. The three-dimensional structure in which the wax forms may be influenced by a mixing ratio of the oil and wax and/or a type of the oil.

In the present invention, it has been found that when the oil-wax gel comprising silicone oil and a wax is used, an oil-wax gel capable of effectively inducing diffuse reflection of light is formed even if the oil-wax gel does not contain conventionally used powder, thereby being applicable to a cosmetic composition for concealing wrinkles. Specifically, when an oil-wax gel is formed by combining 5 to 95 parts by weight of the silicone oil and 1 to 50 parts by weight of the wax, the particles inside the oil-wax gel cause the diffuse reflection effectively, thereby resulting in an excellent effect of concealing the wrinkles temporarily when the oil-wax gel is applied to a wrinkled area.

Additionally, hardness is a factor which may influence not only the feeling of use of the cosmetic composition, but also achievement of the wrinkle-concealing effect by filling in unevenness of the skin. In the present invention, it has been confirmed that when the hardness of the oil-wax gel is 100 dyn/cm$^2$ to 4000 dyn/cm$^2$, the feeling of use is excellent when applied to the skin, and the wrinkled area may be effectively filled in, resulting in an excellent wrinkle-concealing effect.

Accordingly, the present invention may provides a cosmetic composition without powder, which causes the diffuse reflection of light at a wrinkled area and effectively fills the wrinkled area of the skin, thereby enabling temporary wrinkle concealment. Additionally, because powder is not used, the cosmetic composition has an excellent feeling of use when applied to the skin and has prolonged adhesion to the skin, with no white turbidity.

As described above, the present invention may provide a cosmetic composition for concealing wrinkles which comprises the oil-wax gel comprising silicone oil and wax.

In the present invention, 5 to 95 parts by weight of the silicone oil and 1 to 50 parts by weight of the wax may be combined to form an oil-wax gel which induces the diffuse reflection of light more effectively. If a content ratio is not within said range, the degree of diffuse reflection of light is reduced, and as a result, the wrinkle-concealing effect may be inadequate and the hardness suitable for skin application may not be obtained.

As an example, a content of the silicone oil may be 5 to 95 parts by weight, specifically, 10 to 80 parts by weight, more specifically 15 to 70 parts by weight, still more specifically 20 to 55 parts by weight, and still even more specifically 30 to 50.5 parts by weight, relative to 1 to 50 parts by weight of the wax. If the content exceeds 95 parts by weight, the oil-wax gel completely crumbles away, and therefore, the effect of concealing the wrinkle may not appear, or stability of the formulation may be decreased significantly. In contrast, if the content is below 5 parts by weight, the hardness becomes too high, making the application to the skin difficult.

As another example, a content of the wax may be 1 to 50 parts by weight, specifically 2.5 to 20 parts by weight, more specifically 5 to 18.5 parts by weight, still more specifically 7.5 to 15 parts by weight, still more specifically 7.5 to 12.5 parts by weight, relative to 5 to 95 parts by weight of the silicone oil. If the content is below 1 part by weight, the oil-wax gel is not formed and its stability decreases significantly. If the content exceeds 50 parts by weight, the hardness becomes too high to be applied to the skin.

As described above, a proper range of the hardness may directly affect the wrinkle-concealing effect. In the present invention, considering the wrinkle-concealing effect and applicability to the skin, a proper range of the hardness may be 100 dyn/cm$^2$ to 4000 dyn/cm$^2$ as described above, preferably 500 dyn/cm$^2$ to 2500 dyn/cm$^2$, more preferably 700 dyn/cm$^2$ to 2000 dyn/cm$^2$, still more preferably 900 dyn/cm$^2$ to 1200 dyn/cm$^2$, most preferably 1000 dyn/cm$^2$. In a case where the hardness is outside the above range, specifically when the hardness exceeds 4000 dyn/cm$^2$, it becomes heavy and hard to apply to the skin. Additionally, when the hardness is less than 100 dyn/cm$^2$, phase separation and deterioration in feeling of use are displayed.

As used herein, the term "silicone oil" refers to a liquid polymerized siloxane compound having an organic side chain. There are various silicone oils depending on a type of the organic side chain.

The silicone oil may be included in an amount of 5 wt % to 95 wt % relative to the total weight of the oil-wax gel. When the silicone oil content falls within the above range, the wrinkle-concealing effect may be excellent and the hardness may be appropriate.

In the present invention, the silicone oil may be a cyclic silicone oil, linear silicone oil, or silicon oil in which one or more functional groups are substituted. Specifically, the silicone oil may be one or more selected from the group consisting of cyclopentasiloxane, cyclomethicone, cyclotetrasiloxane, cyclohexasiloxane, cycloheptasiloxane, decamethylcyclopentasiloxane, cyclotetrasiloxane, cyclotrisiloxane, dimethicone, capryldimethicone, caprylyl trimethicone, caprylyl methicone, cetearylmethicone, hexadecylmethicone, hexylmethicone, lauryl methicone, myristyl methicone, phenyl methicone, stearyl methicone, stearyl dimethicone, trifluoropropyl methicone, cetyl dimethicone, polyphenylmethylsiloxane, dimethylpolysiloxane, methylphenylpolysiloxane, methyltrimethicone, diphenylsiloxyphenyl trimethicone, and phenyl trimethicone, but is not limited thereto. In other words, the silicone oil in the present invention may be used independently or in a combination of two or more.

In an exemplary embodiment of the present invention, the silicone oil may be a combination of the cyclic silicone oil and linear silicone oil. Using such combination of the cyclic silicone oil and linear silicone oil may be advantageous for formation of a three-dimensional structure suitable for inducing the diffuse reflection of light and/or adjustment of an appropriate hardness of the oil-wax gel.

In another exemplary embodiment of the present invention, the silicone oil may be cyclopentasiloxane and a combination of silicone oils in addition to cyclopentasiloxane. When cyclopentasiloxane and other silicon oils besides cyclopentasiloxane are used, it is advantageous for formation of a three-dimensional structure suitable for inducing the diffuse reflection of light and/or adjustment of appropriate hardness of the oil-wax gel.

As used herein, the term "cyclopentasiloxane" is a type of the silicone oil, of which IUPAC name is decamethylcyclopentasiloxane.

In the present invention, when an oil-wax gel was formed by using cyclopentasiloxane and dimethicone as silicone oil, the diffuse reflection of light was induced and the wrinkle-concealing effect was confirmed to be excellent (Examples 1 to 4).

The cyclopentasiloxane may be included in an amount of 30 wt % to 50 wt %, preferably 35 wt % to 45 wt % relative to the total weight of the oil-wax gel.

The other silicone oils in addition to cyclopentasiloxane may be included in an amount of 1 wt % to 40 wt %, preferably 5 wt % to 35 wt %, more preferably 10 wt % to 30 wt %, relative to the total weight of the oil-wax gel.

As used herein, the term "wax" refers to a milk component which is in a solid phase at room temperature, for example, an alcohol fatty acid ester which is insoluble in water. The wax may be included in a content of 1 wt % to 50 wt % relative to the total weight of the oil-wax gel. If the wax content is below 1 wt %, an oil-wax gel is not formed, whereas if it exceeds 50 wt %, an oil-wax gel is formed with hardness which is too high, making its application to the skin impossible.

As used herein, wax may be at least one selected from the group consisting of mineral wax selected from the group consisting of ceresin wax, paraffin wax, vaseline wax, petroleum wax, ozokerite, montan wax, and microcrystalline wax; animal wax selected from the group consisting of beeswax and lanolin; vegetable wax selected from the group consisting of candelilla, ouricurry, carnauba wax, Japan wax, cocoa butter, cork fiber, and sugarcane wax; hydrogenated oil which is solid at 25° C.; fatty ester and glyceride; synthetic wax selected from the group consisting of polyethylene wax and wax obtained by the Fischer-Tropsch synthesis; and silicone wax, but is not limited thereto. In other words, the wax in the present invention may be used independently or in a combination of two or more.

In an exemplary embodiment of the present invention, the wax may be ceresin wax.

In another exemplary embodiment of the present invention, the wax may be a combination of ceresin wax and other waxes.

As used herein, the term "ceresin wax", as a white or yellow waxy material obtained by purifying the ozokerite, is mainly used as a binding agent or thickening agent in cosmetics.

In the present invention, when an oil-wax gel was formed by using the ceresin wax as wax, the diffuse reflection of light was effectively induced (Examples 1 to 4). Additionally, by further adding one or more of the waxes other than the ceresin wax, degree of the diffuse reflection of light (including the following wrinkle-concealing effect) and/or appropriate hardness of the oil-wax gel may be controlled.

The ceresin wax may be included in an amount of 1 wt % to 50 wt %, preferably 5 wt % to 20 wt % relative to the total weight of the oil-wax gel.

The waxes other than the ceresin wax may be included in an amount of 1 wt % to 20 wt %, preferably 2.5 wt % to 15 wt %, more preferably 5 wt % to 10 wt %, relative to the total weight of the oil-wax gel.

In the present invention, the above cosmetic composition may not contain powder. Because powder is not used, the cosmetic composition has an excellent feeling of use when applied to the skin and prolonged adhesion to the skin, with no white turbidity.

In the present invention, the powder is at least one selected from the group consisting of Silica, PMMA, Alumina, Talk, Mica, Barium sulfate (BaSO4), Titanium dioxide (TiO2), Zinc oxide (ZnO) and Boron nitride, but is not limited thereto.

In the present invention, the oil-wax gel may further comprise an emollient. The emollient may be used for controlling the feeling of use of the oil-wax gel.

The emollient may be included in an amount of 1 wt % 30 wt %, preferably 2.5 wt % to 25 wt %, more preferably 5 wt % to 20 wt %, relative to the total weight of the oil-wax gel.

In the present invention, the emollient may be at least one selected from the group consisting of natural or synthetic triglyceride, ester oil, and hydrocarbon oil.

Examples of the natural or synthetic triglyceride are C8 to C12 acid triglyceride, C12 to C18 acid triglyceride, caprylic/capric triglyceride, caprylic/capric/lauric triglyceride, C10 to C40 isoalkyl acid triglyceride, and C10 to C18 triglyceride, but are not limited thereto.

Examples of the ester oil are ascorbyl palmitate, ascorbyl linoleate, ascorbyl stearate, distearyl maleate, benzyl benzoate, benzyl laurate, butylene glycol dicaprylate/dicaprate, butylene glycol diisononanoate, butylene glycol laurate, butylene glycol stearate, butyl isostearate, cetearyl isononanoate, cetearyl nonanoate, cetyl caprylate, cetyl ethyl hexanoate, cetyl isononanoate, ethylhexyl caprylate/caprate, ethylhexyl isononanoate, ethylhexyl isostearate, ethylhexyl laurate, hexyl laurate, octyldodecyl isostearate, isopropyl isostearate, isostearyl isononanoate, isostearyl isostearate, isocetyl ethylhexanoate, neopentyl glycol dicaprate, neopentyl glycol diethylhexanoate, neopentyl glycol diisononanoate, neopentyl glycol diisostearate, pentaerythrityl stearate, pentaerythrityl tetraethylhexanoate, and triethylhexanoin, but are not limited thereto.

Examples of the hydrocarbon oil are fluid paraffin (liquid paraffin and mineral oil), paraffin, vaseline, microcrystalline wax, and squalene, but are not limited thereto.

In the present invention, the oil-wax gel may further comprise a silicone elastomer. The silicone elastomer may be used for controlling the feeling of use of the oil-wax gel.

The silicone elastomer may be included in an amount of 1 wt % to 30 wt %, preferably 2.5 wt % to 25 wt %, more preferably 5 wt % to 20 wt %.

In the present invention, the silicone elastomer may be at least one selected from the group consisting of dimethicone crosspolymer, cetearyl dimethicone crosspolymer, cetearyldimethicone/vinyldimethicone crosspolymer, dimethicone/vinyldimethicone crosspolymer, dimethicone/PEG-10 crosspolymer, dimethicone/PEG-15 crosspolymer, dimethicone/polyglyceryl-3 crosspolymer, dimethicone/silsesquioxane copolymer, dimethicone/phenylvinyl dimethicone crosspolymer, vinyl dimethicone/lauryl dimethicone crosspolymer, dimethicone/bis-isobutyl PPG-20 crosspolymer, PEG-12 dimethicone/PPG-20 crosspolymer, lauryl dimethicone PEG-15 crosspolymer, lauryl dimethicone/polyglycerin-3 crosspolymer, and polysilicon-11, but is not limited thereto.

As another aspect, the present invention provides a cosmetic product for concealing wrinkles, which comprises the above cosmetic compositions and is formulated in the form of a solid, O/W emulsion, W/O emulsion, W/O/W emulsion, O/W/O emulsion, or water dispersion.

The cosmetic composition may comprise an oil-wax gel or a wax.

In the cosmetic composition for concealing wrinkles according to the present invention, 0.1 wt % to 70 wt % of an oil phase which forms the O/W emulsion may be used relative to the total weight of the composition, and a stable emulsion may be formed within the range.

The oil phase may comprise the oil-wax gel of the present invention.

In order to formulate the emulsion, the cosmetic composition for concealing wrinkles according to the present invention may further comprise a surfactant. The surfactant may be included in the oil phase.

The surfactant may influence a size of emulsified particles, stability of emulsification, and the feeling of use according to a type and content of the surfactant. As the surfactant, a synthetic surfactant or natural surfactant may be used independently or in a combination of two or more. Specifically, an anionic surfactant, cationic surfactant, amphoteric surfactant, or non-ionic surfactant may be used as the surfactant.

The non-ionic surfactant may be sorbitan monostearate, ceteareth-20, sorbitan sesquistearate, sorbitan sesquiolite, lipophilic glyceryl stearate, octyldodeceth-16, polysorbate 20, polysorbate 40, polysorbate 60, polysorbate 65, polysorbate 80, polysorbate 85, polyoxyethylene hydrogenated castor oil, or PEG-PPG copolymer, but is not limited thereto.

Additionally, the non-ionic surfactant includes dimethicone copolyol as an organically modified organopolysiloxane. The organopolysiloxane may be a polydimethylsiloxane modified to include a polyether chain including a polyethylene oxide chain, a polypropylene oxide chain, a mixture thereof, or a moiety derived from both ethylene oxide and propylene oxide; or alkyl-modified dimethicone copolyol containing a C2 to C30 pendant side chain, but is not limited thereto.

Dimethicone copolyol and other silicon-based surfactants may be an additional modification of a polydimethylsiloxane polyether copolymer having a polyethylene oxide pendant side chain, polydimethylsiloxane polyether copolymer having a polypropylene oxide pendant side chain, polydimethylsiloxane polyether copolymer having a mixed polyethylene oxide and polypropylene oxide pendant side chain, polydimethylsiloxane polyether copolymer having a mixed poly(ethylene) (propylene) oxide pendant side chain, polydimethylsiloxane polyether copolymer having a organic betaine pendant side chain, polydimethylsiloxane polyether copolymer having a carboxylate pendant side chain, polydimethylsiloxane polyether copolymer having a quaternary ammonium pendant side chain, or a copolymer having a pendant C2 to C30 linear, branched, or cyclic alkyl moiety, but are not limited thereto.

Additionally, the dimethicone copolyol may be lauryl dimethicone copolyol, lauryl polydimethylsiloxyethyl dimethicone copolyol, dimethicone copolyol acetate, dimethicone copolyol adipate, dimethicone copolyol amine, dimethicone copolyol behenate, dimethicone copolyol butyl ether, dimethicone copolyol hydroxystearate, dimethicone copolyol isostearate, dimethicone copolyol laurate, dimethicone copolyol methyl ether, dimethicone copolyol phosphate, or dimethicone copolyol stearate, but is not limited thereto.

The anionic surfactant may be sodium laurate, sodium palmitate, sodium lauryl sulfate, potassium lauryl sulfate, triethanolamine salt of POE-lauryl sulfate, sodium POE-lauryl sulfate, sodium lauroyl sarcosine, sodium N-myristoyl-N-methyl-taurine, sodium N-cocoyl-N-methyl taurate, sodium lauroyl methyl taurate, sodium POE-oleyl ether phosphate, sodium POE-stearyl ether phosphate, sodium di-2-ethylhexyl sulfosuccinate, sodium monolauroyl monoethanolamidopolyoxyethylene sulfosuccinate, sodium lauryl polypropylene glycol sulfosuccinate, sodium linear-dodecylbenzenesulfonate, monosodium N-lauroyl glutamate, disodium N-stearoyl glutamate, monosodium N-myristoyl-L-glutamate, hardened coconut oil fatty acid ester, POE-alkyl ether carboxylate salt, POE-alkyl aryl ether carboxylate salt, α-olefin sulfonate salt, higher fatty acid ester sulfonate salt, secondary alcohol sulfate ester salt, higher fatty acid alkylolamide sulfate ester salt, sodium lauroyl monoethanolamidosuccinate, N-palmitoyl aspartate di-triethanolamine salt, or sodium caseinate, but is not limited thereto.

The cationic surfactant may be stearyl trimethyl ammonium chloride, lauryl trimethyl ammonium chloride, distearyl dimethyl-ammonium chloride, poly(N,N'-dimethyl-3,5-methylene piperidinium) chloride, cetylpyridinium chloride, alkyl tetraammonium salt, alkyldimethylbenzene ammonium salt, alkyl isoquinolinium salt, dialkyl morpholinium salt, POE-alkylamine, alkylamine salt, polyamine fatty acid derivative, amyl alcohol fatty acid derivative, benzalkonium chloride, or benzethonium chloride, but is not limited thereto.

The amphoteric surfactant may be sodium 2-undecyl-N, N,N-(hydroxyethylcarboxymethyl)-2-imidazoline, disodium 2-cocoyl-2-imidazolinium hydroxide-1-carboxyethyloxy, 2-heptadecyl-N-carboxymethyl-N-hydroxyethyl imidazolinium betaine, lauryl dimethylamino acetate betaine, alkyl betaine, amide betaine, or sulfobetaine, but is not limited thereto.

In the cosmetic product for concealing wrinkles according to the present invention, an aqueous phase forming the W/O emulsion may be used in an amount of 0.1 wt % to 70 wt % relative to the total weight of the composition, for improvement of refreshment and moisture of the cosmetic product.

The aqueous phase may comprise a water-soluble component capable of having skin moisture retention, nutrition, smooth feeling of use, low-temperature stability, or efficacy, and may be water, a polyol, a polymer compound, urea, a moisturizer, or a carbomer, but is not limited thereto.

The polyol may be used as a humectant, and may be glycerin, dipropylene glycol, butylene glycol, pentylene glycol, methylpropanediol, sorbitol, diglycerin, erythritol, pentaerythritol, polybutylene glycol-10, polyglycerin-3, polyglycerin-4, polyglycerin-6, polyglycerin-10, polyglycerin-20, polyglycerin-40, sorbeth-5, sorbeth-6, sorbeth-20, sorbeth-30, sorbeth-40, inositol, maltitol, maltose, mannan, mannitol, mannose, lactitol, lactose, dehydroxypropyl PG-glucoside, dithiaoctanediol, fructose, glucamine, methyl glucamine, glucose, 1,2,6-hexanethiol, methyl gluceth-10, methyl gluceth-20, ozonized glycerin, phytantriol, thioglycerin, threitol, trimethylolpropane, or xylitol, but is not limited thereto.

The cosmetic composition according to the present invention may be prepared by a conventional method used in the art.

In the present invention, the cosmetic compound for concealing wrinkles and the cosmetic product comprising the same may further comprise a fragrance.

The fragrance may be included in an amount of 0.01 wt % to 1.00 wt % relative to the total weight of the cosmetic product.

The cosmetic product may further comprise one or more cosmetically acceptable carriers to be blended in a general skin cosmetic composition, and as a conventional component, for example, oil, water, a surfactant, a humectant, lower alcohol, a thickener, a chelating agent, a pigment, a preservative, and a fragrance may be blended appropriately, but it is not limited thereto.

As another aspect, the present invention provides a method for concealing wrinkles comprising applying the cosmetic composition to skin.

The cosmetic composition and the wrinkle concealing are as described above.

It was confirmed in an exemplary embodiment of the present invention that when applied to an eye area of adult men and women, the cosmetic composition of the present invention showed an excellent wrinkle concealing effect (Table 3). When applied to the back of a hand, the composition was observed to effectively conceal the wrinkles compared to before application (FIG. 5). Accordingly, it was confirmed that a method for concealing wrinkles comprising applying the cosmetic composition of the present invention can be provided.

Advantageous Effects

The cosmetic composition for concealing wrinkles according to the present invention causes diffuse reflection of light at a wrinkled area without using powder and effectively fills the wrinkled area of skin, thereby enabling a temporary concealment of the wrinkle. Because powder is not used, the cosmetic composition has an excellent feeling of use when applied to the skin and prolonged adhesion to the skin, with no white turbidity.

DESCRIPTION OF DRAWINGS

FIG. 1 is a graph showing changes in wrinkle depths (the result of the wrinkle-concealing effects) upon application of the oil-wax gel according to an exemplary embodiment.

FIG. 2 is a graph showing changes in number of wrinkles (the result of the wrinkle-concealing effects) upon application of the oil-wax gel according to an exemplary embodiment.

FIG. 3 is a graph showing changes in wrinkle lengths (the result of the wrinkle-concealing effects) upon application of the oil-wax gel according to an exemplary embodiment.

FIG. 4 is a graph showing changes in roughness (the result of the wrinkle-concealing effects) upon application of the oil-wax gel according to an exemplary embodiment.

FIG. 5 is images comparing the wrinkle-concealing effects before and after the application of the oil-wax gel according to an exemplary embodiment.

BEST MODE

Hereinbelow, the present invention will be described in detail with accompanying exemplary embodiments. However, the exemplary embodiments disclosed herein are only for illustrative purposes and should not be construed as limiting the scope of the present invention.

Examples 1 and 2, and Comparative Examples 1 to 3: Preparations of Oil-Wax Gel and Oil Powder Cosmetic Component Each ingredient was mixed according to the ratios shown in Table 1 below, dissolved by heating at 80° C., and then cooled to room temperature to prepare an oil-wax gel (Examples 1 and 2, and Comparative Examples 1 and 2) and an oil-powder cosmetic component (Comparative Examples 3).

TABLE 1

| Ingredients | (wt %) | | | | |
|---|---|---|---|---|---|
| | Example 1 | Example 2 | Comparative Example 1 | Comparative Example 2 | Comparative Example 3 |
| 1. Cyclopentasiloxane | To 100 | To 100 | To 100 | To 100 | To 100 |
| 2. Dimethicone | 10 | 10 | 10 | 10 | 10 |
| 3. Hexyldecyl ethylhexanoate (ester oil) | 10 | 10 | 10 | 10 | 10 |
| 4. Dimethicone/vinyl dimethicone crosspolymer (silicone elastomer) | 10 | 10 | 10 | 10 | 10 |
| 5. Ceresin wax | 20 | 20 | 0.5 | 55 | |
| 6. Microcrystalline wax | | 20 | | | |
| 7. Silica | | | | | 20 |

Experimental Example 1: Measurement of Hardness of Oil-Wax Gel

Hardness of the oil-wax gels prepared in Examples 1 and 2, and Comparative Examples 1 to 3 was measured and shown in Table 2 below. The hardness up to the depth of 2 mm of a sample was measured using adapter #3, a Fudoh Rheometer RT-3005D model of Rheotec Co, at an operation speed of 2 cm/min. After five measurements, an average value was derived.

TABLE 2

| | Example 1 | Example 2 | Comparative Example 1 | Comparative Example 2 | Comparative Example 3 |
|---|---|---|---|---|---|
| Hardness (dyn/cm²) | 2490 | 3120 | 60 | 5000 | Unmeasurable |

In Examples 1 and 2, when applied to the skin, the oil-wax gel showed its wrinkle-concealing effect while effectively filling in the uneven skin caused by wrinkles. In contrast, when the oil-wax gel of Comparative Example 1 was applied to the skin, the oil-wax gel thereof completely crumbled away, and therefore, it was not possible to achieve the wrinkle-concealing effect. In the case of the oil-wax gel of Comparative Example 2, which had high hardness, it was difficult to apply it to the skin. On the other hand, in the case of the oil-powder cosmetic component obtained from the composition rate of Comparative Example 3, it was able to be applied to the skin, but failed to provide an excellent feeling of use.

Experimental Example 2: Investigation of Wrinkle-Concealing Effect Through Image Analysis The oil-wax gel of Example 1 was applied to the eyes of seven adult males and females. In addition, the wrinkle-concealing effect was measured through image analysis using PRIMOS lite (GFM). Specifically, it was evaluated in terms of wrinkle depth, wrinkle length, number of wrinkles, and roughness.

The results are shown in Table 3 below and FIGS. 1 to 4.

TABLE 3

| | Wrinkle Depth (μm) | Wrinkle Length (μm) | No. of Wrinkles | Roughness (μm) |
|---|---|---|---|---|
| Before use | 60.00 | 203.00 | 341.67 | 33.10 |
| After use | 55.33 | 185.67 | 279.00 | 31.90 |
| Reduction Rate (%) | 7.78 | 8.54 | 18.34 | 3.63 |

The oil-wax gel of Example 1 was shown to have an excellent wrinkle-concealing effect in terms of the wrinkle depth, wrinkle length, number of wrinkles, and roughness.

Experimental Example 3: Comparison of the Wrinkle-Concealing Effects of Example 1 and Comparative Example 3

Usability of the cosmetic composition of Example 1 and Comparative Example 3 was tested on 16 volunteers aged in their 30s to 50s who have problems with their wrinkles. Test items were wrinkle concealment, white turbidity, caking up, agglomeration, dryness, and satisfaction, and 0 to 5 points were given for each item. The average score results are shown in Table 4 below.

TABLE 4

| Items | Example 1 | Comparative Example 3 |
|---|---|---|
| Wrinkle concealment | 4.6 | 4.4 |
| White turbidity | 4.7 | 3.8 |
| Dryness | 4.2 | 3.5 |
| Caking up | 3.9 | 3.6 |
| Agglomeration | 4.3 | 4.1 |
| Satisfaction | 4.5 | 3.9 |

As shown above, the oil-wax gel of Example 1 had a better wrinkle-concealing effect and a higher score for all other items, i.e., white turbidity, dryness, caking up, and agglomeration, compared to that of Comparative Example 3, which contains a large amount of powder.

Comparative Example 4: Preparation of Cosmetic Composition for Concealing Wrinkles, Containing Powder The cosmetic composition of Comparative Example 4 was prepared according to the ratios shown in Table 5 below. The oil phases of items 1 to 7 were heated and dissolved at 70° C. in a separate container. Items 11 and 12 were added to the aqueous phase of items 8 to 10 to disperse sufficiently at room temperature, and heated to 70° C. to mix with the oil phase. The aqueous phase was then emulsified (primary) with a homogenizer at 70° C. After introducing item 15 dissolved in a small amount of purified water, the resultant was emulsified (secondary) and then cooled to 50° C. After introducing well-dispersed item 14 into item 13, the resultant was then emulsified (tertiary) and cooled to room temperature to prepare the cosmetic composition.

TABLE 5

| | Components | Content (wt %) |
|---|---|---|
| 1. | Cetearyl alcohol | 1.00 |
| 2. | Shea butter | 8.00 |
| 3. | Caprylic/capric triglyceride | 8.00 |
| 4. | Glyceryl stearate | 1.00 |
| 5. | PEG-100 stearate | 1.00 |
| 6. | Polyglyceryl-3 methylglucose distearate | 2.00 |
| 7. | Dimethicone | 12.00 |
| 8. | Distilled water | Up to 100 |
| 9. | Glycerin | 5.00 |
| 10. | Trisodium EDTA | 0.02 |
| 11. | Xanthan gum | 0.10 |
| 12. | Carbopol | 0.30 |
| 13. | Distilled water | 15.00 |
| 14. | Silica | 15.00 |
| 15. | Neutralizing agent | 0.30 |

Experimental Example 4: Comparison of Wrinkle-Concealing Effects of Example 1 and Comparative Example 4

Usability of the cosmetic composition of Example 1 and Comparative Example 4 was tested on 16 volunteers aged in their 30s to 50s who have problems with their wrinkles. Test items were wrinkle concealment, white turbidity, caking up, agglomeration, dryness, and satisfaction, and 0 to 5 points were given for each item. The average score results are shown in Table 6 below.

TABLE 6

| Items | Example 1 | Comparative Example 4 |
|---|---|---|
| Wrinkle concealment | 4.6 | 4.4 |
| White turbidity | 4.7 | 3.8 |
| Caking up | 3.9 | 3.6 |
| Agglomeration | 4.3 | 4.1 |
| Dryness | 4.2 | 3.5 |
| Satisfaction | 4.5 | 3.9 |

As shown above, the oil-wax gel of Example 1 had a better wrinkle-concealing effect and a higher score for all items, i.e., white turbidity, caking up, agglomeration, and dryness, compared to that of Comparative Example 4, which contains a large amount of powder.

Experimental Example 5: Application Test of Cosmetic Composition Comprising Oil-Wax Gel The cosmetic composition of Example 1 for concealing wrinkles was applied to the back of a hand, and then the wrinkle-concealing effects were observed before and after the application. As a result, as shown in FIG. 5, it was confirmed that the cosmetic composition comprising the oil-wax gel according to the present invention effectively concealed the wrinkles.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. Furthermore, the scope of the present invention is defined by the appended claims rather than the detailed description, and it should be understood that all modifications or variations derived from the meanings and scope of the present invention and equivalents thereof are included in the scope of the appended claims.

The invention claimed is:

1. A method for concealing wrinkles comprising applying a cosmetic composition comprising:
    an oil-wax gel for diffusing reflection of light at a wrinkled area to a skin,
    wherein the oil-wax gel is a gel comprising silicone oil and wax,
    wherein hardness of the oil-wax gel is 100 to 4000 dyn/cm$^2$, and
    wherein the oil-wax gel comprises 5 to 95 parts by weight of the silicone oil relative to 100 parts by weight of the oil-wax gel and 1 to 50 parts by weight of the wax relative to 100 parts by weight of the oil-wax gel.

2. The method of claim 1, wherein the silicone oil is at least one selected from the group consisting of cyclopentasiloxane, cyclomethicone, cyclotetrasiloxane, cyclohexasiloxane, cycloheptasiloxane, decamethylcyclopentasiloxane, cyclotetrasiloxane, cyclotrisiloxane, dimethicone, capryldimethicone, caprylyl trimethicone, caprylyl methicone, cetearylmethicone, hexadecylmethicone, hexylmethicone, lauryl methicone, myristyl methicone, phenyl methicone, stearyl methicone, stearyl dimethicone, trifluoropropyl methicone, cetyl dimethicone, polyphenylmethylsiloxane, dimethylpolysiloxane, methylphenylpolysiloxane, methyltrimethicone, diphenylsiloxyphenyl trimethicone, and phenyl trimethicone.

3. The method of claim 1, wherein the wax is at least one selected from the group consisting of:
    mineral wax selected from the group consisting of ceresin wax, paraffin wax, vaseline wax, petroleum wax, ozokerite, montan wax, and microcrystalline wax;
    animal wax selected from the group consisting of beeswax and lanolin;
    vegetable wax selected from the group consisting of candelilla, ouricurry, carnauba wax, Japan wax, cocoa butter, cork fiber, and sugarcane wax;
    hydrogenated oil which is solid at 25° C.;
    fatty ester and glyceride;
    synthetic wax comprises polyethylene wax; and
    silicone wax.

4. The method of claim 1, wherein the oil-wax gel further comprises an emollient.

5. The method of claim 4, wherein the emollient is comprised in an amount of 1 wt % to 30 wt % relative to 100 wt % by weight of the oil-wax gel.

6. The method of claim 4, wherein the emollient is at least one selected from the group consisting of natural or synthetic triglyceride, ester oil, and hydrocarbon oil.

7. The method of claim 1, wherein the oil-wax gel further comprises silicone elastomer.

8. The method of claim 7, wherein the silicone elastomer is comprised in an amount of 1 wt % to 30 wt % relative to 100 wt % by weight of the oil-wax gel.

9. The method of claim 7, wherein the silicone elastomer is at least one selected from the group consisting of dimethicone crosspolymer, cetearyl dimethicone crosspolymer, cetearyldimethicone/vinyldimethicone crosspolymer, dimethicone/vinyldimethicone crosspolymer, dimethicone/polyethylene glycol (PEG)-10 crosspolymer, dimethicone/PEG-15 crosspolymer, dimethicone/polyglyceryl-3 crosspolymer, dimethicone/silsesquioxane copolymer, dimethicone/phenylvinyl dimethicone crosspolymer, vinyl dimethicone/lauryl dimethicone crosspolymer, dimethicone/bis-isobutyl polypropylene glycol (PPG)-20 crosspolymer, PEG-12 dimethicone/PPG-20 crosspolymer, lauryl dimethicone PEG-15 crosspolymer, lauryl dimethicone/polyglycerin-3 crosspolymer, and polysilicon-11.

10. The method of claim 1, wherein the cosmetic composition is formulated in a form of a solid, oil (O)/water (W) emulsion, W/O emulsion, W/O/W emulsion, O/W/O emulsion, or water dispersion.

11. The method of claim 1, wherein the oil is placed in an inner space of wax crystals, wherein the wax comprises ceresin wax in an amount of 5 wt % to 50 wt % relative to 100 wt % by weight of the oil-wax gel, wherein the cosmetic composition does not contain powder.

12. The method of claim 11, wherein the powder is at least one selected from the group consisting of silica, polymethyl methacrylate (PMMA), alumina, Talc, mica, barium sulfate ($BaSO_4$), titanium dioxide ($TiO_2$), zinc oxide (ZnO) and boron nitride.

* * * * *